United States Patent [19]

Andrews et al.

[11] Patent Number: 5,103,325
[45] Date of Patent: Apr. 7, 1992

[54] SEGMENTED HOLOGRAM FOR MULTI-IMAGE DISPLAY

[75] Inventors: John R. Andrews, Fairport; Michael D. Rainsdon, Walworth; Werner E. Haas, Webster, all of N.Y.

[73] Assignee: Xerox Corporation, Stamford, Conn.

[21] Appl. No.: 591,238

[22] Filed: Oct. 1, 1990

[51] Int. Cl.$^5$ .................. G03H 1/26; G02F 1/1335
[52] U.S. Cl. .......................... 359/23; 340/765; 359/22; 359/95
[58] Field of Search .................. 350/3.76, 3.6, 337, 350/339 F, 348, 3.75; 340/765

[56] References Cited

U.S. PATENT DOCUMENTS

| | | |
|---|---|---|
| 3,614,426 | 10/1971 | Donzelle . |
| 3,832,027 | 8/1973 | King . |
| 4,206,965 | 6/1980 | McGrew ............... 350/3.76 |
| 4,364,627 | 12/1982 | Haines ................ 350/3.76 |
| 4,372,639 | 2/1983 | Johnson ............... 350/3.7 |
| 4,421,380 | 12/1983 | McGrew ............... 350/3.78 |
| 4,506,956 | 3/1985 | Dir ................... 350/339 F |
| 4,509,818 | 4/1985 | Prikryl ............... 350/3.76 |
| 4,527,864 | 7/1985 | Dir ................... 350/337 |
| 4,670,744 | 6/1987 | Buzak . |
| 4,834,476 | 5/1989 | Benton . |
| 4,896,929 | 1/1990 | Haas et al. . |
| 4,964,684 | 10/1990 | Iovine ................ 350/3.76 |

OTHER PUBLICATIONS

Andrews et al., "Holographic Stereograms Generated with a Liquid Crystal Spatial Light Modulator," Spie, vol. 902, Three Dimensional Imaging and Remote Sensing Imaginig, 15 Jan. 1988, pp. 92 to 94.

Primary Examiner—Bruce Y. Arnold
Assistant Examiner—Martin Lerner
Attorney, Agent, or Firm—Finnegan, Henderson, Farabow, Garrett & Dunner

[57] ABSTRACT

A holographic display includes "segmented" images configured as if positioned in separate viewing "cells" corresponding spatially to preselected subareas of a desired display area with invisible segmenting cell sides. In one embodiment, a polarized conjugate reference light source projects the segmented hologram images form a light-transmissive recording medium into the display area, a multi-element nematic 90° twisted shutter assembly changes the polarization of light emanating from subareas corresponding to the images to be blocked while keeping unchanged the polarization of the segmented images to be displayed, and a sheet polarizer positioned between the multi-element shutter and the viewer blocks from view images from those subareas which the polarization direction has been changed by the multi-element shutter. In other embodiments, light-reflective recording mediums and multi-element nematic shutters having an appropriate guest-host dyes are used. Constantly viewable unsegmented holographic images recorded in the same recording medium as the segmented images or on a separate recording medium can be multiplexed into the display area using a conjugate light source of a different frequency or having a different polarization condition (e.g., unpolarized) from the conjugate light source used to project the segmented images to be selectively displayed/blocked.

32 Claims, 7 Drawing Sheets

MASTER SLIT HOLOGRAM

SEGMENTED HOLOGRAM FOR MULTI-IMAGE DISPLAY

BACKGROUND OF THE INVENTION

1. Field of the Invention

The field of the present invention is holographic displays, specifically holographic displays with multiple images, including methods and apparatus for achieving such displays.

2. Description of the Prior Art

Holographic displays, including holographic displays using a stereographically recorded holographic images, are known to be useful for applications where the design and evaluation of complex structures such as homes, offices and automobiles require the presentation or evaluation of three dimensional designs See, for example, U.S. Pat. Nos. 3,832,027 to King and 4,834,476 to Benton. Such holographic images can be synthesized from a plurality of computer-generated two-dimensional views and then stereographically recorded on a recording medium. The holographic images in the developed recording medium can then be projected into a display area for evaluation by a viewer who, at least to some extent, is able to view different portions of the three-dimensional image by moving in relation to the display area. In this fashion, the viewer is able to see different aspects of the image in proper perspective leading to a better appreciation of the spatial relationships of parts of the image.

Recently, holographic displays have been used for man-machine interfaces in order to present, for example, the operational status of various parts of a copier machine. See U.S. Pat. No. 4,896,929 (Haas et al.). The problem in using holographic displays in traditional man-machine interfaces is to display all of the information of interest while not having the holographic image cluttered with too much information. Liquid crystal or LED pointers can highlight certain parts of an image though cluttering an image may still reduce the effectiveness of the display. While color and reference beam angle multiplexing might be used to show separately several images, each of which contains different information, thus reducing the density of information in any single image, a reduced diffraction efficiency and intermodulation impose a practical limit on the number of separate multiplexed images to four or less for typical copier-printer displays. Because such applications traditionally require at least 30 separate pieces of information to be displayed, the problem of a cluttered display still exists.

Simply blocking or masking part of a holographic image created in the conventional manner such as with a twisted nematic liquid crystal display is not very effective in simplifying the display for at least two reasons. First, the blocked areas are dark, distracting from the rest of the display. Second, and of particular significance, the liquid crystal display or other masking element exists only in one plane. Therefore, as a viewer changes viewing position with respect to the display it is possible to see objects lying behind the blocked plane, the so-called "look around" effect. This effect is not aesthetically pleasing and ultimately leads to confusion as to the meaning of the blocked portions of the display.

SUMMARY OF THE INVENTION

As a consequence of the above, it is an object of the present invention to provide a holographic image display wherein one or more of a plurality of holographic images can be selectively displayed or blocked from view, while preventing "look around".

It is a further object of the present invention to provide a holographic display which can discriminate between holographic images to be selectively displayed or blocked from view and contiguous holographic images to be continuously displayed in the display apparatus.

Additional objects and advantages of the present invention will be apparent from the following detailed description of the preferred embodiments thereof, which proceed with reference to the accompanying drawings.

In view of the aforesaid objects, and in accordance with the invention as embodied and broadly described herein, the apparatus for selectively displaying discrete holographic images in respective subareas of a display area comprises a holographic recording medium having a plurality of segmented holographic images stereographically recorded therein. The images are spatially separated in the medium to correspond to the subareas and each is configured as if bounded by imaginary segmenting planes extending to the rear of the display area with respect to the viewer. The apparatus further includes a reference light means including a first reference light for illuminating the holographic recording medium to project the plurality of segmented holographic images into the display area. The apparatus also includes masking means including shutter means positioned between the display area and the viewer and having shutter elements commensurate in extent with the subareas for selectively blocking from view, including "look around" view, one or more of the plurality of projected segmented images.

Preferably, the masking means includes first polarizing means for causing the light from the reference light means that illuminates the holographic medium to be polarized in one direction; the shutter means includes second polarizing means for changing the direction of the polarization of the light emanating from the subareas corresponding to the segmented images to be blocked; and the masking means further includes third polarizing means positioned between the shutter means and the viewer, for transmitting only light polarized in the one direction. The shutter elements are individually activatable to change the polarization of light passing therethrough. The shutter means can preferably be a multi-element twisted nematic type liquid crystal shutter having elements commensurate in extent with the subareas, and the first and third polarizing means can be sheet polarizers.

It is alternatively preferred that the masking means includes means for causing the light incident upon the recording medium from the reference light means to be of a certain color, and means for absorbing light of the certain color emanating from those subareas corresponding to the discrete segmented images to be blocked from view. The color absorbing means can preferably include a multi-element nematic type liquid crystal shutter with individually activatable shutter elements commensurate in extent with the subareas and having an appropriate guest-host dye.

It is further preferred that the holographic record medium include at least one unsegmented overlay image recorded therein using a recording light spatially separated from the recording light used to record the segmented images. In this case, the reference light means includes a second reference light correspondingly spatially separated from the first reference light and being unpolarized. Alternatively, the overlay image can be recorded in a second recording medium and illuminated by the same reference light used to illuminate the recording medium having the segmented images.

Further in accordance with the present invention, as embodied and broadly described herein, the apparatus for use in a holographic display comprises a recording medium having a plurality of discrete segmented holographic images stereographically recorded in spatially separated medium subareas. Each of the discrete images is configured for viewing as if bounded by imaginary segmenting planes extending in a direction away from the plane of the medium with respect to a viewer. Preferably, the recording medium is an image plane master.

Still further in accordance with the present invention, as embodied and broadly described herein, the method for selectively displaying discrete holographic images in respective subareas of a display area and blocking from view, including "look around" view, other holographic images within the area comprises the steps of forming a hologram in the display area by illuminating a recording medium having recorded therein each of the holographic images positioned within, and segmented to correspond to, a respective one of the subareas; and masking the subareas corresponding to the other segmented images for selectively blocking from view the segmented images in those subareas. The forming step further comprises configuring a plurality of imaginary cells each having a transparent cell opening commensurate with the respective subarea and opaque, segmenting cell planar sides extending to the rear of the plane of the cell opening with respect to the viewer; generating a sequence of 2-D perspective representations of the images positioned within the respective cells, the representations corresponding to vantage points traversing the display area, the generating step including removing from each representation all parts of images not observable through the cell opening from the respective vantage point by virtue of the segmenting cell sides; and recording stereographically the plurality of 2-D representations in a holographic recording medium in sequential order.

It is also preferred that the hologram forming step includes the further substep of stereographically recording in the holographic medium at least one unsegmented overlay image. Also, the projecting step includes the step of projecting the segmented images separately from the overlay image, and the masking step includes discriminating between the segmented images to be selectively blocked and any portions of the overlay image appearing in the display subareas corresponding to the one or more segmented images to be blocked.

It is further preferred that the masking step include polarizing in one direction the light illuminating the recording medium, selectively changing the polarization of the light emanating from the subareas corresponding to the segmented images to be blocked to another direction, and subsequently filtering the light emanating from the display area to the viewer to transmit only light polarized in the one direction. The polarization changing step can be carried out using a multi-element twisted nematic type liquid crystal shutter with individually activatable shutter elements commensurate in extent with the subareas.

It is alternatively preferred that the method includes illuminating the recording medium with light of a certain frequency (color), and the masking step includes absorbing light of that certain frequency (color) emanating from those subareas corresponding to the segmented images to be blocked from view. The color absorbing step can be carried out with a multi-element twisted nematic type liquid crystal shutter with individually activatable shutter elements commensurate in extent with the subareas and having an appropriate guest-host dye.

BRIEF DESCRIPTION OF THE DRAWINGS

FIGS. 4–7B are schematic representations of the various steps in forming a segmented hologram in accordance with the present invention;

Reference will now be made to present preferred embodiments of the invention which are illustrated in the above-described accompanying drawings.

DESCRIPTION OF THE PREFERRED EMBODIMENTS

Figure 1:
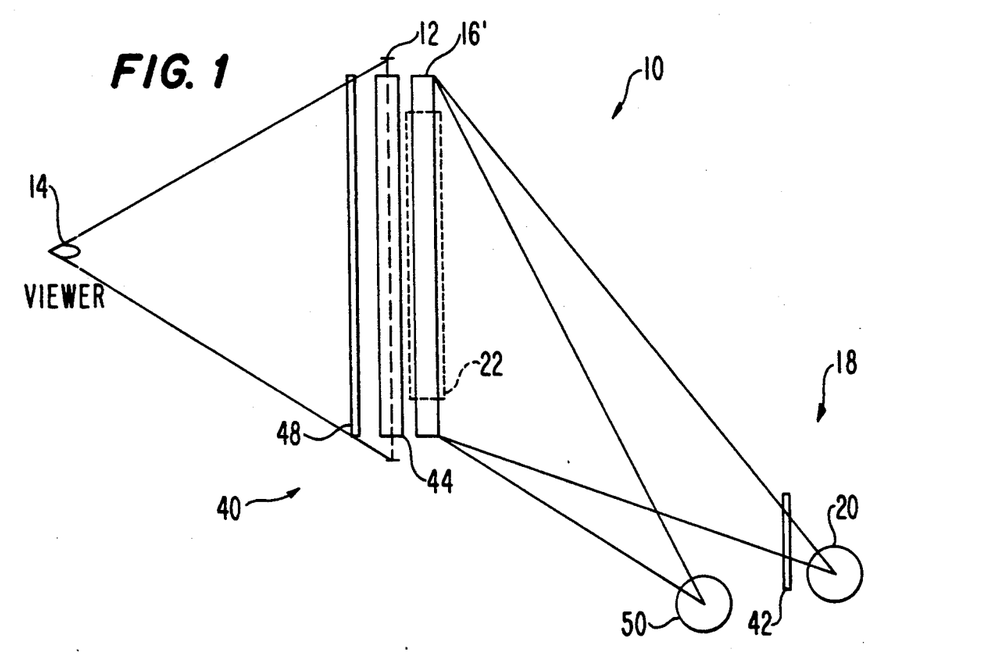
FIG. 1 is a schematic side view of apparatus made in accordance with the present invention for selectively displaying holographic images using light transmissive holography.

With reference initially to FIG. 1 there is shown schematically apparatus 10 for selectively displaying discrete ones of a plurality of holographic images in an image display area, such as display area 12, relative to viewer 14, while blocking from view the other holographic images. Importantly, the images blocked from view by apparatus made in accordance with the present invention are blocked from "look around" view, such as might otherwise occur if the viewer changed position, e.g. moved horizontally with respect to the display area 12 (into or out of the plane of the paper for the FIG. 1 representation). A sharper overall display results with little or no blocked image residue visible for oblique lines of sight.

Figure 3A:
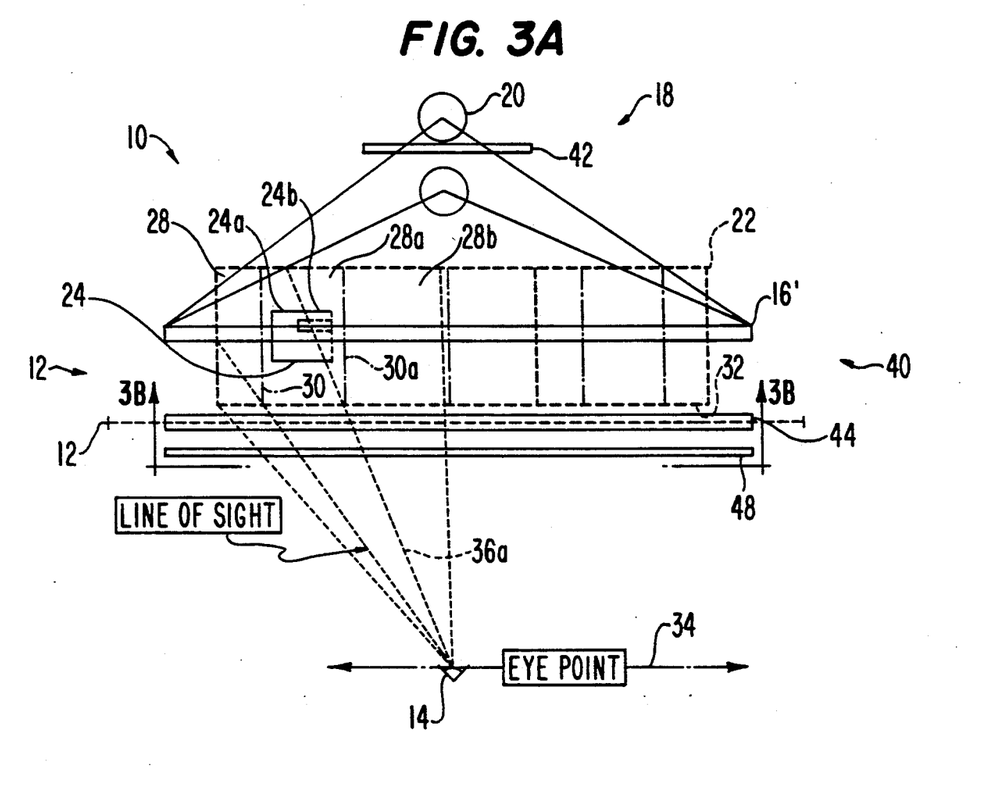
FIG. 3A is a top plan view of the embodiment pictured in FIG. 1.
Figure 3B:
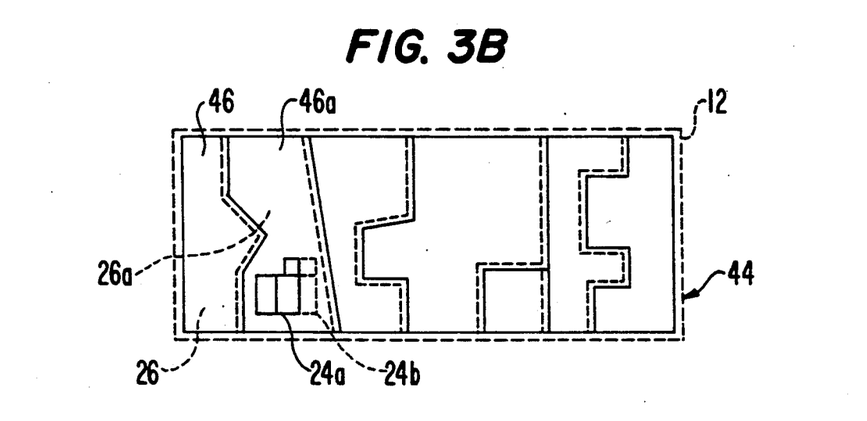
FIG. 3B is a sectional front view of the FIG. 1 apparatus taken at the line 3B—3B in FIG. 3A.

In accordance with the present invention, the apparatus for selectively displaying discrete holographic images includes a holographic recording medium having holographic images stereographically recorded therein. The images are spatially separated in the recording medium corresponding to predetermined subareas and are "segmented", that is, configured in a manner to be discussed in more detail hereinafter as if bounded by invisible but opaque imaginary segmenting planes extending to the rear of the display area with respect to the viewer. As embodied herein, and with reference to FIGS. 1 and 3, apparatus 10 includes developed holographic recording medium 16' positioned in display area 12 which can, for example, be the display area on a copier control panel. Of course, the present invention is not intended to be limited by such an application but only by the appended claims and their equivalents.

Further in accordance with the present invention, the apparatus includes holographic image display means including reference light means having a first reference light for illuminating the holographic recording medium to project into the display area. As embodied herein and with continued reference to FIGS. 1 and 3, apparatus 10 includes image display means with reference light means 18 having a first conjugate reference light 20. The segmented holographic images recorded within medium 16', when illuminated by reference light 20, appear as holographic images in image volume 22 (shown dotted in FIGS. 1 and 3A) closely adjacent or surrounding display area 12. Only one such image (schematic 24 of a copier) is shown in FIG. 3A but the illustrated embodiment has the capacity for 7 segmented images, one in each of 7 display subareas 26, 26a, etc. (see FIG. 3B). The images in each display subarea 26, 26a can be selectively displayed or blocked from view. Apparatus made in accordance with the present invention can accommodate a greater or lesser number of segmented images, as will be appreciated from the succeeding discussion, so that the present invention is not intended to be limited by the number of segmented images or subareas shown in the above embodiment.

The segmented images, including image 24, are generated by a method to be described in more detail hereinafter, to appear as if they were positioned in separate "cells" such as cells 28, 28a, etc. formed by opaque segmenting side planes 30, 30a, etc. which extend away from the front surface 32 of image volume 22 with respect to viewer position 14. As depicted in FIG. 3B, the front edges of segmenting planes 30, 30a etc. coincide with the boundaries of subareas 26, 26a etc. For the depicted viewer position 14 in FIG. 3A, image 24 would appear as if truncated by segmenting side plane 30a. In other words, the image presented to the viewer at position 14 would correspond to the image portion 24a to the left of line of sight 36a while the truncated portion 24b corresponding to the image portion to the right of line of sight 36a would not be seen. Horizontal movement of the viewer along line 34 in FIG. 3A would cause a correspondingly different viewed image to be seen, with different fractions of "full image" 24 being visible. Thus, the recorded segmented images such as segmented image 24, can be thought of as being "viewable" only through the "cell opening" afforded by the respective portions of image volume front surface 32 corresponding to the respective subarea 26, 26a. As a consequence, each of the segmented images recorded in holographic recording medium 16' can be totally blocked from view by shutter means having elements commensurate in extent with the respective subareas and located at the position of front surface 32.

Further in accordance with the present invention, the holographic image display means includes masking means with shutter means having individual shutter elements for selectively blocking from view, including "look around" view, one or more of the projected segmented images. As embodied herein, as shown in FIGS. 1 and 3, masking means 40 includes first polarizing means 42 positioned to polarize the light incident on holographic recording medium 16' from conjugate reference light 20. Polarizing means 42 can be a sheet polarizer which is known to pass light polarized in one preferred direction.

As further embodied herein, masking means 40 also includes shutter means 44 which, in the depicted embodiment, is a multi-element 90° twisted nematic type liquid crystal assembly. The elements 46 of assembly 44 constitute a second, selective polarizing means in the disclosed embodiment and are configured to be commensurate in extent with subareas 26, 26a, etc. of display area 12. Elements 46, 46a, etc. are individually and selectively electrically activatable between an "on" state where no change in polarization of light passing through the element occurs and an "off" state where the polarization of light passing through the element is changed. As depicted in FIGS. 3A and 3B, element 46a is in the "on" state such that no change in polarization occurs in the light emanating from image portion 24a, causing image portion 24a to be viewable by a viewer at 14 for reasons that will be made apparent through the subsequent discussion. Image portion 24a (but not portion 24b) is depicted in the FIG. 3B representation because the view is presumed to correspond to the FIG. 3A viewer position 14. Although shown spaced from front surface 32 of image volume 22, assembly 44 is at or closely adjacent surface 32 so that is acts as a multi-element shutter to control polarization of light emanating from images in volume 22 in the direction of viewer 14 even for oblique lines of sight.

As further embodied herein, masking means 40 includes third polarizing means 48 positioned between the viewer and multi-element shutter means 44. Polarizing means 48, which can be a sheet polarizer, is oriented to pass light polarized in the same direction as first polarizing means 42. Light emanating from any of the projected segmented images to be blocked from view would have a polarization different from the polarization direction of polarizing means 48 and thus the segmented image would not reach the viewer. To selectively display an image such as image portion 24a, the polarizing element 46a of assembly 44 corresponding to subarea 26a in which image portion 24a resides, would be electrically activated to the "on" state for a nematic type liquid crystal element. Light emanating from the image portion 24a would be polarized in the same direction as first polarizing means 42 and thus would pass third polarizing means 48 and be seen by the viewer at position 14.

Preferably, the selective image display apparatus of the present invention also can include means for concurrently displaying one or more unsegmented, "overlay" images in the display area. Such an overlay image would be useful to frame or arrange the segmented images as, for example, in a copier control display where the overlay image would comprise a perspective outline of the copier and the segmented images would comprise components having potential malfunctions appropriately positioned with respect to the overall copier image. Such an overlay image would be visible throughout the display area 12 irrespective of the condition (display/block) of the segmented images in the subareas 26, 26a if the illumination source for the overlay holographic image is unpolarized in the case of the FIG. 1 embodiment or, in the general case, unaffected by the masking means. In this sense, the masking means of the present invention discriminates between the overlay images and the segmented images to be blocked, even if located in the same subarea.

As embodied herein and with reference again to FIG. 1, developed holographic recording medium 16' has recorded therein one or more overlay images in a multiplexed arrangement. In the depicted embodiment, the overlay images are multiplexed using a recording light source spatially separated from the recording light source used to record the segmented discrete images, such as copier image 24. Apparatus 10 also includes a second conjugate reference light source 50 to project the overlay images into display volume 22. Second light source 50 is correspondingly spatially separated from the first reference light source 20 used to project the segmented discrete images.

In the above embodiment, light from second light source 50 used to project the overlay image is not polarized. Consequently, light emanating from the overlay image projected into image volume 22 will always have light components polarized in a direction to pass polarizing means 48 and thus be seen by the viewer at 14, whether or not the polarization direction of the light components are shifted by one or more deactivated nematic shutter elements 46, 46a in assembly 44. In this manner, portions of an overlay image extending into or through a subarea containing a blocked segmented image will be largely unaffected as the masking means 40 effectively discriminates between the overlay and the segmented images to be blocked.

Figure 2:
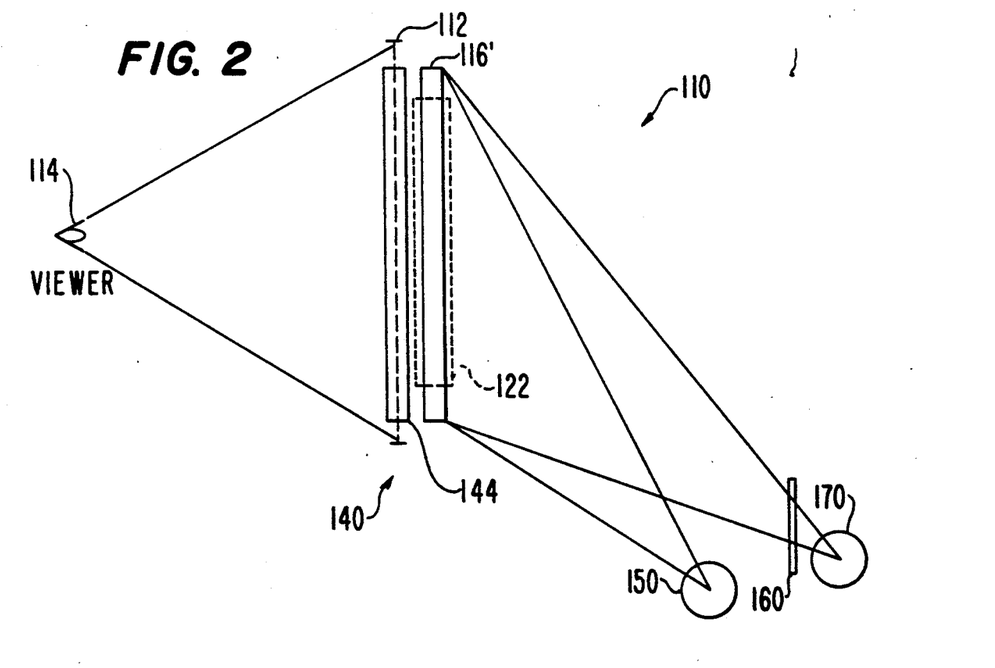
FIG. 2 is a schematic side view of an alternate to the embodiment of the invention pictured in FIG. 1.

FIG. 2 shows a alternative embodiment of the selective image displaying apparatus made in accordance with the present invention, which alternative embodiment is designated generally by the numeral 110. Components similar in function to those described in relation to the FIG. 1 embodiment are designated by numbers with the prefix "100" added thereto. As embodied in FIG. 2, apparatus 110 includes a developed holographic recording medium 116' with segmented images stereographically recorded therein for projection by conjugate reference light 120 into image volume 122 for display in area 112, in a manner similar to that previously discussed. In the FIG. 2 embodiment, however, masking means 140 includes color filter 160 or other means for providing light of a certain frequency (color) for illuminating medium 116' to project the segmented images. Further, masking means 140 includes means for selectively filtering that color component from light emanating from segmented images desired to be blocked. The selective color filtering means can be a multi-element 90° twisted nematic type liquid crystal shutter assembly 144 with an appropriate guest-host dye incorporated into each element.

One skilled in the art also would realize that multiplexed images comprising overlay images and segmented discrete images could be recorded using two light sources of different frequency (color) rather than spatially separated light sources as depicted in the embodiment depicted in FIGS. 1 and 3. As in the first embodiment, an overlay image can be recorded in recording medium 116' and displayed concurrently with the segmented images. The use of a white light or light of a different color (frequency) from a second conjugate light source 150 to project the overlay image will permit other color components of light emanating from the overlay image always to pass multi-element shutter assembly 144 and be viewable irrespective of the "on" or "off" condition of the individual elements 146 in multi-element assembly 144. Although not depicted, apparatus combining the polarizing and color filtering masking techniques can be constructed. Such constructions are intended to come within the scope of the appended claims.

The process for forming the developed holographic recording medium 16' or 116' having the segmented images recorded therein begins, in accordance with the present invention, with the preliminary step of dividing the display area into subareas to correspond to the number and location of requested images to be displayed, and then configuring opaque segmenting planes which form the sides of the "cells" in which the segmented images are to be located, as an open-ended irregular honeycomb-like structure as, for example, is shown in FIGS. 3A and 3B.

In accordance with the present invention, the next step is to generate a series of two dimensional (2-D) perspective representations of all the segmented images, with each image segmented to appear as if located within a respective cell of the honeycomb-like structure, one 2-D representation for each of a plurality of expected viewer viewing positions with respect to the display area. Each generated 2-D representation reflects the images positioned within the cells formed by the segmenting plane/side configuration with the portions of each 2-D image representation not visible through the cell openings from the particular viewing position as a consequence of the segmenting cell sides being deleted from the representation.

It is highly preferred that a Computer Aided Design (CAD) system with multi-layer memory and a "hidden line" or "hidden surface" removal option be used to generate the 2-D segmented perspective representations. A suitable system is available from Intergraph Corp. and was successfully run on a DEC VAX 11/780 computer. Preferably, the generating step includes, for each of a plurality of view positions with respect to the display area, generating perspective projections of the images including the cell sides to eliminate portions of the images not observable due to the cell sides. Thereafter, the cell sides are selectively eliminated from the images to yield the desired segmented images. The segmented 2-D images are then sequentially recorded in series by suitable means, such as by photographing a CRT display or using a film recorder.

Figure 4:
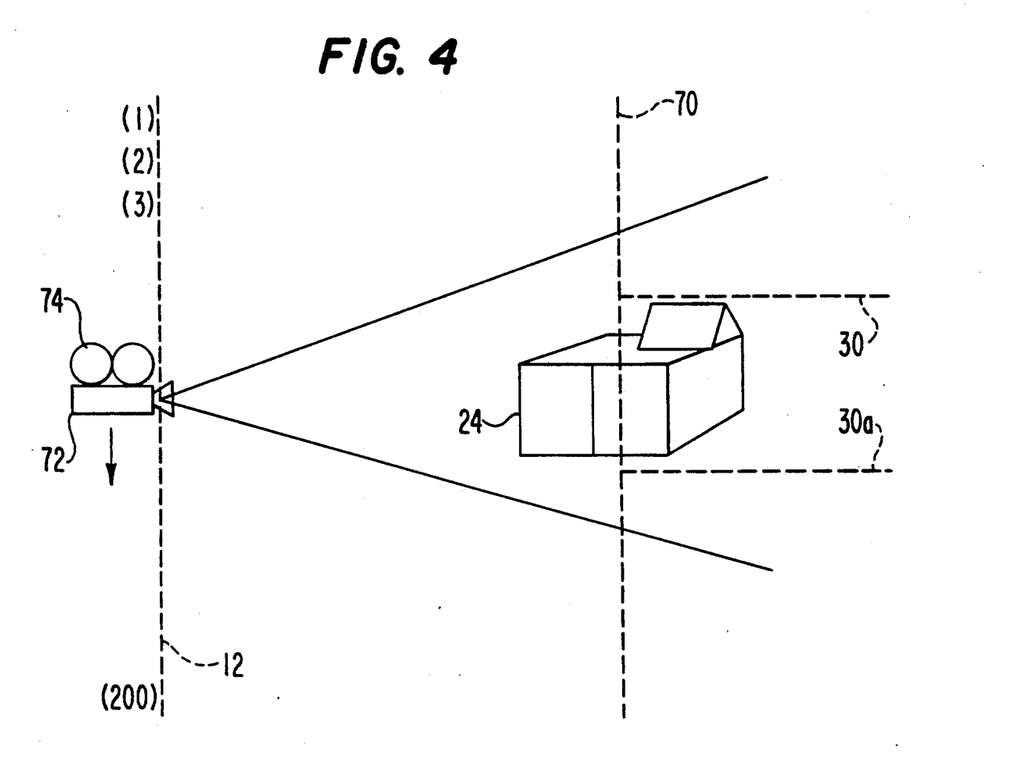

The next step in the process of preparing a holographic medium with segmented images recorded therein is more clearly explained in relation to FIGS. 4 through 8. In accordance with the present invention, the 2-D representations of the segmented images next are stereographically recorded in the holographic medium. As embodied herein and with initial reference to FIG. 4, there is depicted a computer CRT screen designated generally by the numeral 70 on which there is displayed a segmented 2-D representation of the images, such as a copier image 24 discussed previously. The portions of the images not viewable as a result of the segmenting cell side planes such as side planes 30 and 30a are not present in the representations and the cell planes themselves also are not visible in the image appearing on the computer screen. Also shown in FIG. 4 is a schematic representation of camera 72 which can be moved to various positions designated (1), (2), (3), ... (200) corresponding to viewer vantage points traversing display area 12. The camera 72 records the segmented 2-D representations in sequence corresponding to the viewer vantage points and generates a film record 74.

Figure 5A:
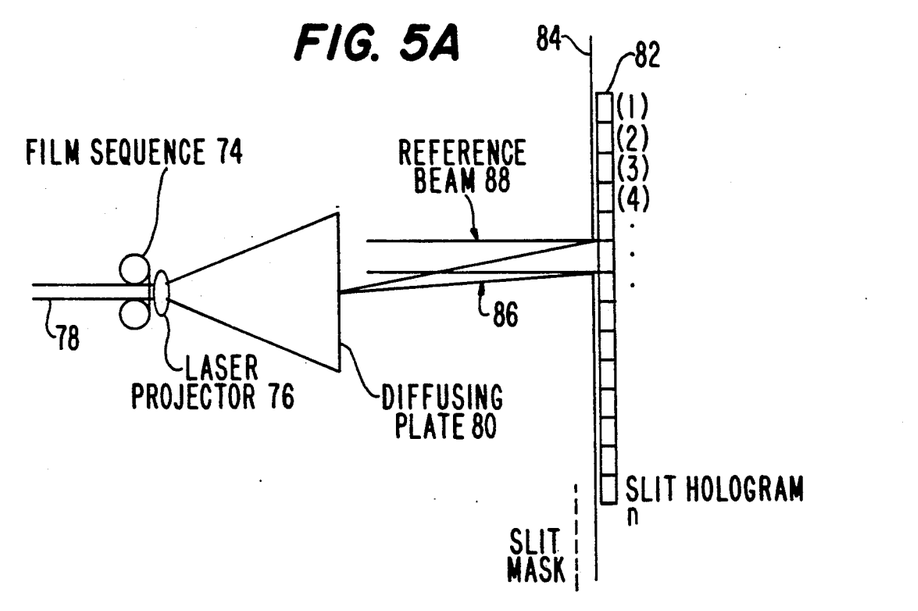
Figure 5B:
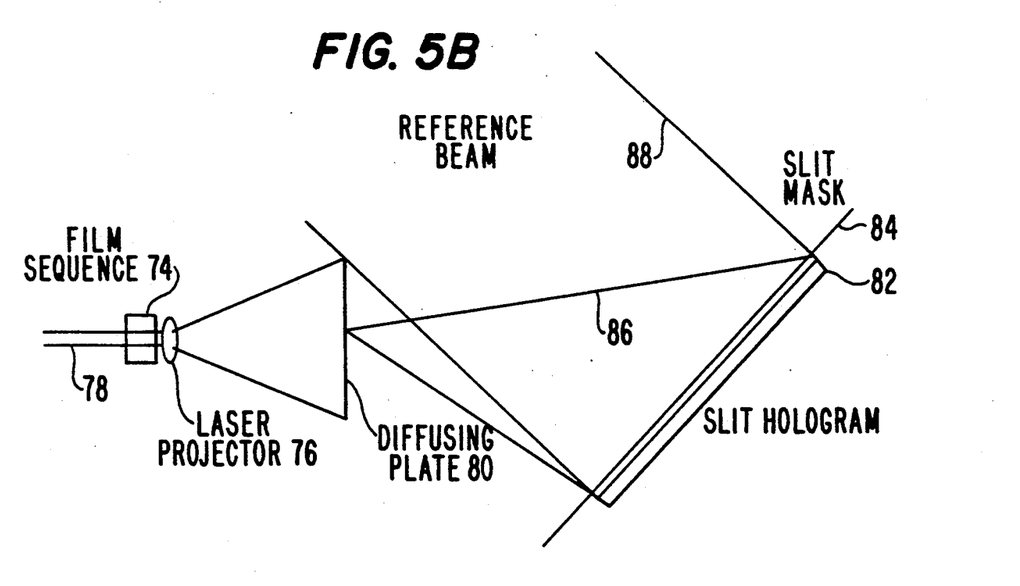

Turning now to FIGS. 5A and 5B, disclosed respectively are a top and side view of stereographic holographic image recording apparatus including laser projector 76 which utilizes film record 74 in the following manner. Each film frame corresponding to the segmented 2-D image representations from a particular viewer vantage point is illuminated by a first portion 78 of a coherent light beam to project the film image on a diffusing plate 80. The image from diffusing plate 80 is then caused to be recorded in a location on holographic recording medium 82 which corresponds to the viewer position 14 with respect to display area 12 in FIG. 1.

Figure 6:
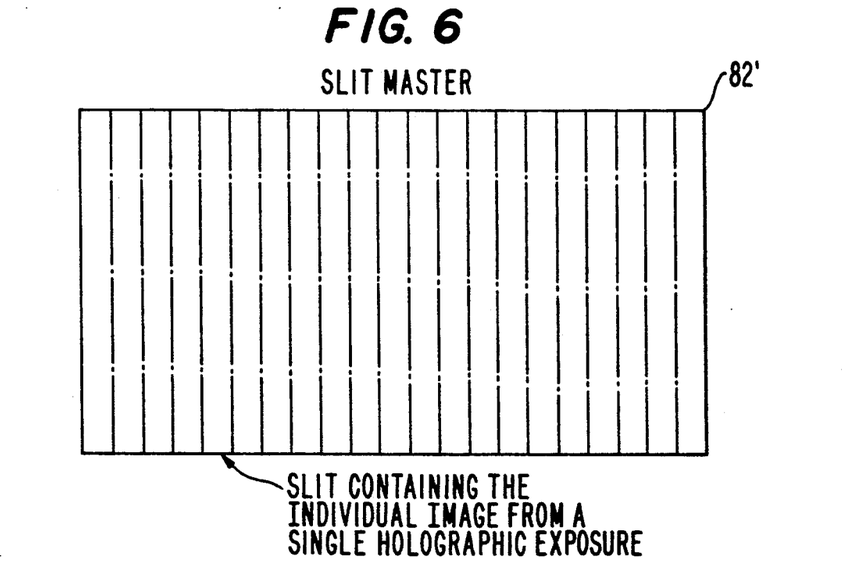

In the depicted apparatus, wherein the segmented 2-D images have been constructed to depict perspective due to horizontal parallax only, the holographic recording medium 82 is masked by slit mask 84 to provide an aperture for recording the image only along a narrow slit. As one skilled in the art would appreciate, the holographic image is created in the holographic recording medium 82 by the light rays 86 emanating from diffusing plate 80 in interference with a second portion 88 of the coherent light beam, the first portion 78 having been used to illuminate a frame from film record 74. FIG. 5B shows that second coherent beam portion 88, referred to as "reference beam" also is incident upon the holographic recording medium 82 through slit mask 84 but at a different angle than the image beam 86 from diffusing plate 80, as is known in the art. The "slit master" resulting from the multiple exposures of holographic recording medium 82 through slits corresponding to different viewer positions traversing the display area is shown schematically in FIG. 6 and designated generally by the reference number 82', with the "prime" reflecting the fact that the recording medium 82 has been developed.

Figure 7A:
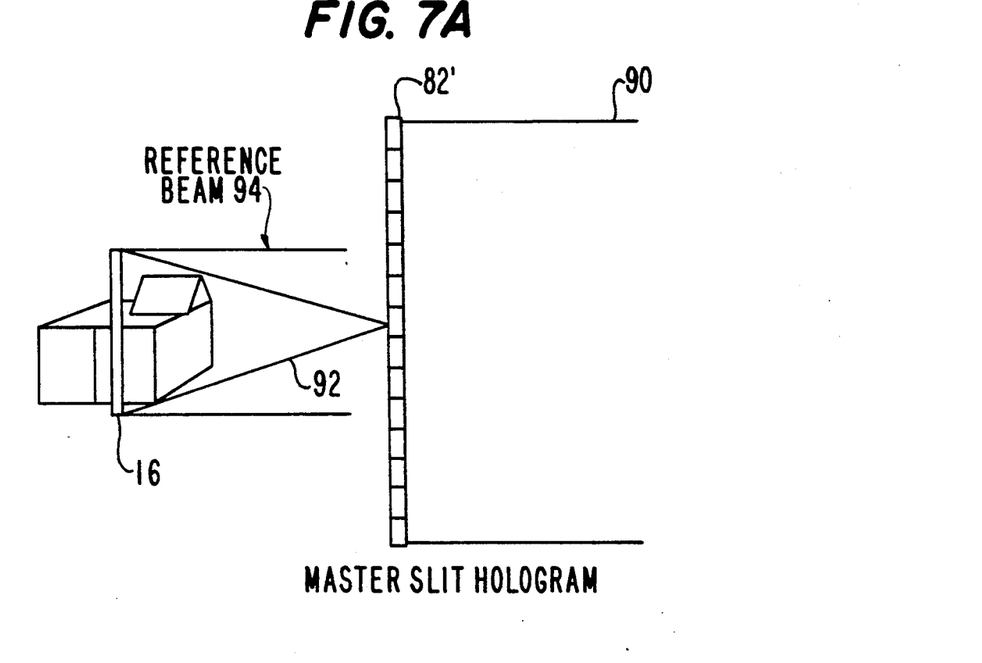
Figure 7B:
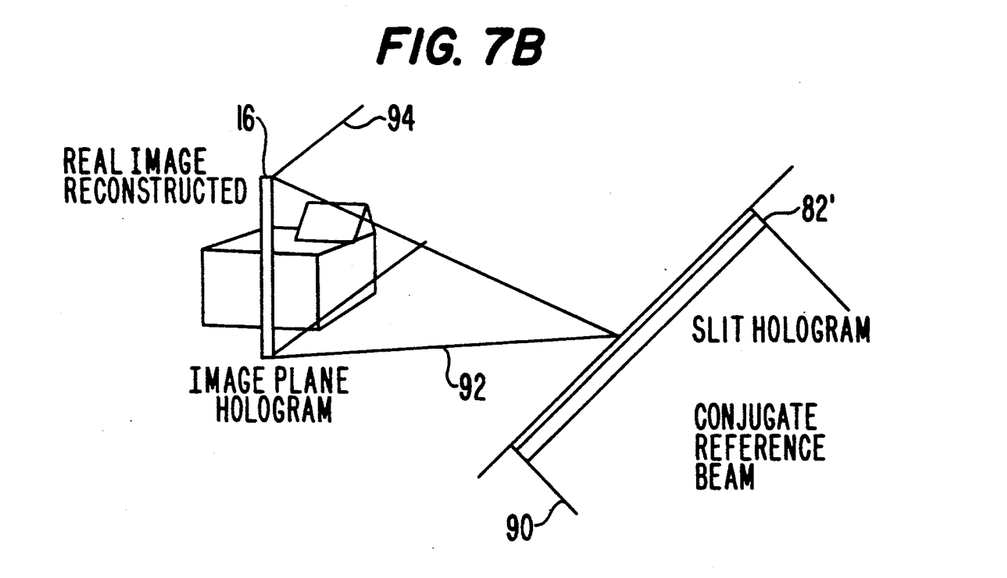

With reference now to FIGS. 7A and 7B, as embodied in the process of the present invention the slit master medium 82' is used to construct image plane master mediums 16' or 116' which are utilized in the displaying apparatus depicted in FIGS. 1-3. In FIGS. 7A and 7B, slit master medium 82' is illuminated by a first part 90 of a beam of coherent light to project rays 92 from the images to recording medium 16. Recording medium 16 is also illuminated with a second part 94 of the same coherent light beam used to illuminate master slit hologram 82' to provide constructive interference with light rays 92, which enables real images to be created in recording medium 16.

Figure 8A:
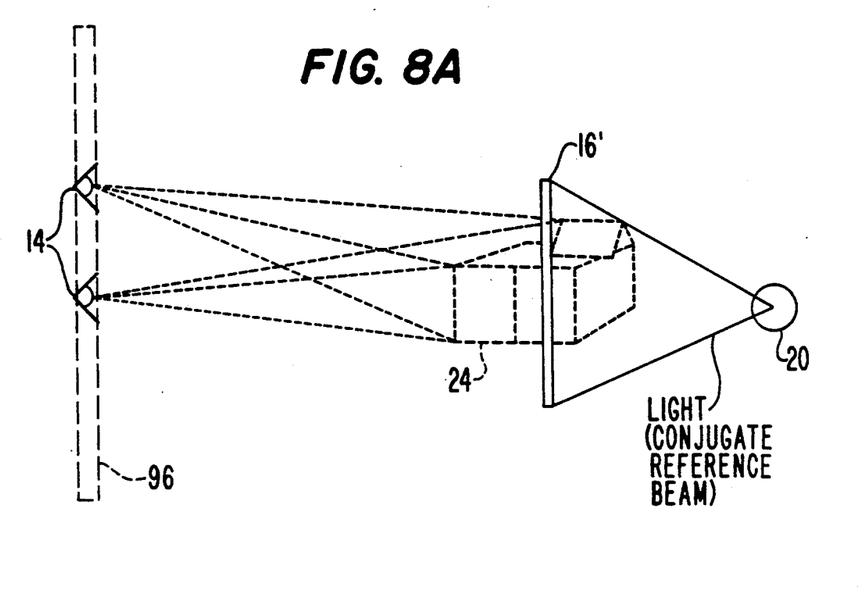
FIGS. 8A and 8B are schematic representations used to explain the positional relationships of the segmented hologram in relation to the viewer.
Figure 8B:
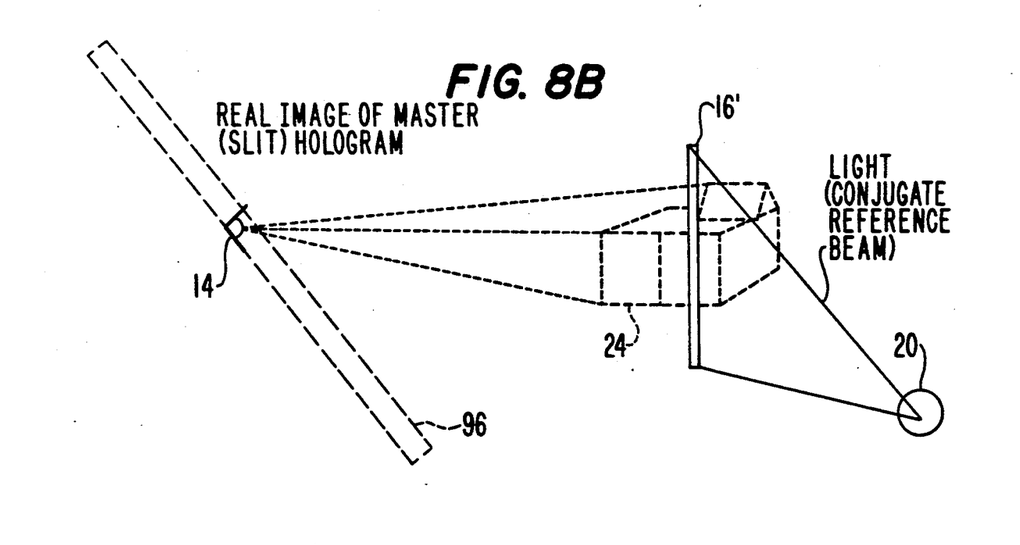

During the image plane master medium recording step depicted FIGS. 7A and 7B, slit master 82' and the image plane recording medium 16 are separated by a distance corresponding approximately to the expected distance between display area 12 and the viewer 14. As depicted schematically in FIGS. 8A and 8B, when the developed holographic recording medium 16' (which is the image plane master) is illuminated by a conjugate reference beam from light source 20, real image 96 of the slit master forms at the position of the viewer 14 enabling the images projected into the image display volume surrounding image plane master 16' to come into focus, as would be understood by one skilled in the art.

Still further in accordance with the invention, the method of selectively displaying discrete holographic images includes illuminating the holographic recording medium with a reference light to project into the display area a hologram containing the plurality of segmented images. As embodied herein, and as discussed previously in relation to the embodiments depicted in FIGS. 1 and 2, appropriating conjugate reference lights 20 or 120 located at positions corresponding to the respective recording light source positions illuminate the respective developed recording medium 16' or 116' and project into display volumes 22 or 122 a hologram containing the plurality of images, such as image 24.

Still further in accordance with the displaying method of the present invention, the projected hologram is masked with masking elements coextensive with the subareas to selectively block from view other segmented images, namely those not intended to be displayed. As embodied herein, the masking step can be carried out using appropriate polarizing apparatus or color filtering apparatus, as described in detail previously, or a combination of both.

The above-described method optionally includes the step of stereographically recording an perspective "overlay" image in the holographic recording and projecting the image into the display area using a different conjugate reference light source. The overlay image also can be generated using a CAD system but need not be segmented as the overlay image is intended to be essentially unaffected by the masking step. As discussed previously, multiplexing using spatially or frequency separated recording and reference light sources for the segmented images and the overlay images allows the masking means to discriminate between these images, being able to selectively block the former but not the latter.

The previous embodiments of the present invention all utilize the known principles of holographic recording mediums of the type that are light-transmissive, that is, wherein the source of illumination used to project the hologram into display area can be on the opposite side of the recording medium with respect to the viewer. However, the present invention also can utilize the principles of recording mediums which are "light-reflective" in a manner which will be understood from the succeeding discussion.

The use of a reflective-type holographic recording medium permits the use of alternative masking means that is, where the masking means is used to mask the light incident on the specific subareas corresponding to the images to be blocked, and thereby preventing entirely the formation of the segmented images to be blocked in the projected hologram. In the previously discussed embodiments, the images to be blocked are part of the projected hologram which utilize masking means to intercept and selectively block light emanating from the images to be blocked. In comparison, the embodiment shown in FIG. 9 and to be discussed henceforth, prevents totally the formation of holographic segmented images corresponding to the images to be blocked and thereby prevents those images from being seen by the viewer.

Figure 9:
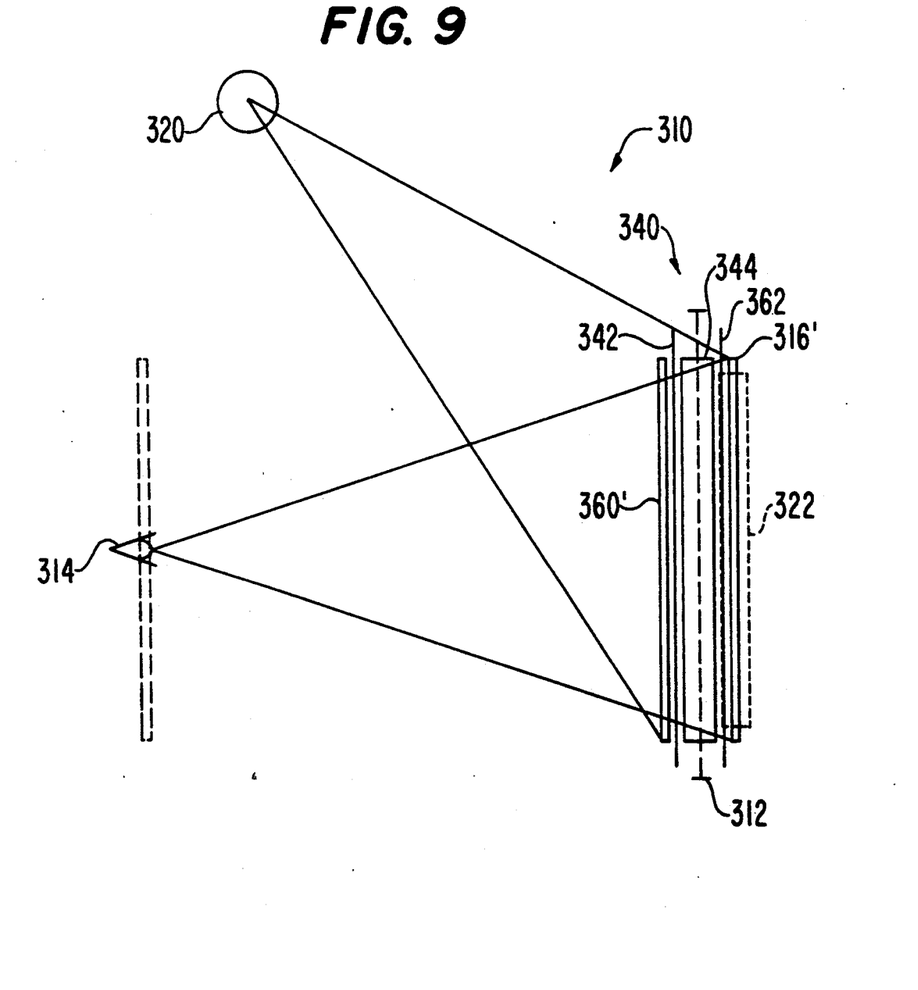
FIG. 9 is a schematic side view representation of another embodiment of the present invention using reflective holography principles.

As shown in FIG. 9 wherein components similar to those in the previously discussed embodiments are designated by the same numeral but with the prefix 300 added thereto, display apparatus 310 includes a reflective-type recording medium 316' for projecting a hologram into volume 322 which is closely adjacent the display area 312. The recording medium 316' is intended to be illuminated by conjugate light source 320 which is located on the same side of the recording medium as viewer 314. The light from conjugate light source 320 is polarized by a sheet polarizer 342 and then is acted upon by a multi-element twisted nematic liquid crystal shutter assembly 344. As in the previous embodiment, the twisted nematic shutter 344 in the FIG. 9 embodiment is a 90° twisted nematic shutter.

Hence, the light incident in the direction of recording medium 316' which passes through the multi-element shutter assembly 344 will be polarized in one direction in those portions passing through activated elements of shutter 344 but will be polarized in a direction 90° different for those portions of the incident light which pass through the shutter elements corresponding to the subareas in which the segmented images to be blocked are located. Disposed between multi-element shutter 344 and the recording medium 316' is another sheet polarizer 362 which filters out the portions of the incident light which are rotated 90°. As the individual elements of multi-element shutter 344 are commensurate in extent with the subareas, the portions of the incident light ordinarily used to project the images to be blocked does not reach recording medium 316', such that holographic images corresponding to the images to be blocked are not generated, and consequently are not seen by the viewer at 314.

Sheet polarizer 362 has the same polarization direction as sheet polarizer 342 and thus light passing through the activated elements of 344 which do not change the polarization, are incident upon recording medium 316' and serve to create the holographic images of the segmented images to be displayed. Also, the light emanating from the segmented images to be displayed can pass back through the activated elements of shutter assembly 344 and the first sheet polarizer 342 and thus be seen by the viewer because the light has the proper polarization to pass through first sheet polarizer 342.

Preferably, a second recording medium 360' in which an overlay image has been recorded is utilized in conjunction with the same conjugate light source 320 to create a holographic overlay image in the display area. The overlay image projected using separate recording medium 360' which is, of necessity, a light-transmissive type recording medium, is largely unaffected by the masking means, and the viewer at position 314 can see the overlay image irrespective of the condition (activated/deactivated) of the individual elements of multi-element shutter assembly 344.

It will be apparent to those skilled in the art that various modifications and variations can be made in the above-described embodiments of the present invention without departing from the scope or spirit of the invention. For example, one skilled in the art would appreciate that other liquid crystal effects can be used for the display, such as the birefringence effect in nematic liquid crystals, the cholesteric-nematic phase transition, and the "supertwist" nematic liquid crystal effect. Thus, it is intended that the present invention cover such modification and variations provided they come within the scope of the appended claims and their equivalents.

What is claimed is:

1. Method for selectively displaying discrete ones of a plurality of holographic images arrayed in respective subareas of a display area and blocking from view, including "look around" view, the others of said holographic images, the method comprising the steps of:
    (a) forming a hologram in the display area, the forming step including the step of illuminating a recording medium having recorded therein each of the plurality of holographic images positioned within, and segmented to correspond to, a respective one of the subareas, to project the hologram into the display area; and
    (b) selectively masking those subareas corresponding to said other segmented images to block from view said other segmented images.

2. The selective holographic image displaying method as in claim 1 wherein said forming step includes the preliminary steps of:
    (i) constructing graphically a plurality of viewing cells having transparent cell openings corresponding to the respective subareas and opaque segmenting cell sides extending away from the opening with respect to a viewer,
    (ii) generating a sequence of 2-D perspective representations of the images positioned within respective viewing cells, the representations corresponding to vantage points traversing the display area, said generating step including removing from each representation all image parts not observable through the cell opening from the respective vantage point by virtue of the segmenting cell sides, and eliminating from each representation the opaque segmenting cell sides, and
    (iii) recording stereographically the plurality of 2-D representations in the holographic recording medium in sequential order.

3. The selective holographic image displaying method as in claim 2 wherein said generating step is carried out using a CAD system having hidden line or hidden surface removal capability, and said generating step includes, for each of a plurality of view positions with respect to the display area, generating perspective projections of the images including the cell sides to eliminate portions of the images not observable due to the cell sides, and then selectively eliminating the cell sides from the images.

4. The selective holographic image displaying method as in claim 1 including the step of forming an unsegmented overlay image in the display area and wherein said masking step discriminates between said other segmented images to be blocked and any portions of the overlay image appearing in the display subareas corresponding to said other segmented images to be blocked.

5. The selective holographic image displaying method as in claim 4 wherein said overlay image was recorded in the same recording medium as the segmented images but using a recording light source spatially separated from the recording light source used to record said segmented images; and wherein said illuminating step includes the step of illuminating the recording medium with correspondingly spatially separate reference light sources.

6. The selective holographic image displaying method as in claim 5 wherein said masking step discriminates on the basis of frequency (color), and wherein said separate light sources are of a different frequency (color).

7. The selective holographic image method as in claim 5 wherein said masking step discriminates on the basis of polarization, and wherein said separate light sources have different polarizations.

8. The selective holographic image displaying method as in claim 4 wherein said overlay image is recorded in a second recording medium and wherein the method includes the step of illuminating the segmented image recording medium and the overlay image recording medium using the same light source.

9. The selective holographic image displaying method as in claim 8 wherein the recording medium is a light-reflective recording medium and the illuminating step includes illuminating the recording medium on the same side as the viewer; wherein said polarization changing step is carried out using a multi-element 90° twisted nematic liquid crystal shutter with individually activatable shutter elements commensurate in extent with respective subareas and said masking step includes activating the shutter elements corresponding to the segmented images to be displayed and deactivating the shutter elements corresponding to the segmented images to be blocked.

10. The selective holographic image displaying method as in claim 1 wherein said masking step includes polarizing in one direction the light used to illuminate the recording medium, selectively changing the polarization of the light emanating from the subareas corresponding to the segmented images to be blocked to another direction, and filtering light emanating from the display area to the viewer to transmit only light polarized in said one direction.

11. The selective holographic image displaying method as in claim 10 wherein the recording medium is a light-transmissive recording medium and said illuminating step includes the step of illuminating the recording medium on the side opposite the viewer; wherein said polarization changing step is carried out using a multi-element 90° twisted nematic liquid crystal shutter with individually activatable shutter elements commensurate in extent with respective subareas and said masking step includes activating the shutter elements corresponding to segmented images to be displayed, and deactivating the elements corresponding to the segmented images to be blocked.

12. The selective holographic image displaying method as in claim 1 wherein said masking step includes polarizing in one direction the illuminating light; selectively changing the polarization of the polarized illuminating light incident on the subareas corresponding to the segmented images to be blocked to another direction; and filtering light incident on the recording medium to transmit only light polarized in said one direction.

13. The selective holographic displaying method as in claim 12 wherein the recording medium is a light-reflective recording medium and the illuminating step includes illuminating the recording medium on the same side as the viewer; wherein said polarization changing step is carried out using a multi-element 90° twisted nematic liquid crystal shutter with individually activatable shutter elements commensurate in extent with respective subareas and said masking step includes activating the shutter elements corresponding to the segmented images to be displayed and deactivating the shutter elements corresponding to the segmented images to be blocked.

14. The selective holographic image displaying method as in claim 13 wherein said color absorbing step is carried out with a multi-element 90° twisted nematic type liquid crystal shutter with individually activatable shutter elements commensurate in extent with the subareas and having an appropriate guest-host dye, and wherein the shutter elements corresponding to the segmented images to be blocked are deactivated.

15. The selective holographic image displaying method as in claim 1 wherein said masking step includes illuminating the recording medium with light of a certain frequency (color), and absorbing light of said certain frequency (color) emanating from those subareas corresponding to the segmented images to be blocked from view.

16. The method as in claim 1 wherein said masking step includes the steps of blocking light corresponding to said other segmented images and transmitting through said those subareas, light not corresponding to said other segmented images.

17. Apparatus for selectively displaying discrete ones of a plurality of holographic images arranged in respective subareas of a display area and blocking from view, including "look around" view, the other holographic images, the apparatus comprising:

(a) a holographic recording medium having a plurality of segmented holographic images stereographically recorded therein, said segmented images being spatially separated in said medium corresponding to the subareas and each comprising only portions of said image visible from within a viewing cell configured with a transparent opening corresponding to a respective subarea and with imaginary, opaque segmenting planes extending away from the display area with respect to a viewer; and (b) holographic image display means including:
  (i) reference light means including a first reference light for illuminating said holographic recording medium to project a hologram into the display area, and
  (ii) means for selectively masking subareas corresponding to said other segmented images to block from view said other segmented images.

18. The apparatus as in claim 17 wherein said masking means includes first polarizing means for polarizing in one direction the illuminating light from said reference light means; second polarizing means for selectively changing the direction of the polarization of the light emanating in the direction of the viewer from said hologram through the subareas corresponding to the segmented images to be blocked; and third polarizing means positioned between said second polarizing means and the viewer, for filtering out the changed polarized light.

19. The apparatus as in claim 18 wherein said recording medium is a light-transmissive medium and is positioned between said first reference light and the viewer; wherein said first polarizing means is located between said first reference light and said recording medium; wherein said second polarizing means is a multi-element 90° twisted nematic liquid crystal shutter having shutter elements commensurate in extent with respective ones of said subareas, each of said shutter elements being individually activatable to change the polarization of light passing therethrough; and wherein said first and said third polarizing means are sheet polarizers.

20. The apparatus as in claim 17 wherein said illuminating light is incident on said recording medium through said subareas; and wherein said masking means includes first polarizing means for polarizing in one direction said illuminating light, second polarizing means for selectively changing the polarization direction of the polarized illuminating light portions incident through the subareas corresponding to said other segmented images to be blocked, and third polarizer means for filtering out incident light with changed polarization.

21. The apparatus as in claim 20 wherein said recording medium is a light-reflective medium, said first reference light being positioned on the same side of the recording medium as the viewer; said second polarizer means is a multi-element 90° twisted nematic liquid crystal shutter having shutter elements commensurate in extent with the subareas, each of said shutter elements being individually activatable to change the polarization of light passing therethrough; said first polarizer means is a sheet polarizer positioned between said first reference light and said multi-element shutter; and said third polarizer means is a sheet polarizer positioned between said multi-element shutter and said recording medium.

22. The apparatus as in claim 17 wherein said recording medium further includes at least one unsegmented overlay image recorded therein using a recording light spatially separated from the recording light used to record said segmented images; said reference light means includes a second reference light correspondingly spatially separated from said first reference light; and said masking means discriminates between light emanating from holographic images formed from said first and second reference lights.

23. The apparatus as in claim 22 wherein said masking means discriminates on the basis of frequency (color), and wherein said first and said second reference lights are of different frequency (color).

24. The apparatus as in claim 22 wherein said masking means discriminates on the basis of polarization, and wherein said first and second reference lights have different polarization.

25. The apparatus as in claim 17 further including a second recording medium having recorded therein at least one unsegmented overlay image, said second recording medium also being illuminated by said first reference light.

26. The apparatus as in claim 25 wherein the recording medium in which the segmented images are recorded is a light-reflective recording medium, the first reference light being on the same side of the light-reflective recording medium as the viewer; wherein said masking means are disposed between said light-reflective recording medium and the viewer; and wherein said second recording medium is a light-transmissive recording means and is disposed between said masking means and the viewer.

27. The apparatus as in claim 17 wherein said masking means includes (i) means for causing the light incident upon said recording medium from said reference light means to be of a certain frequency (color), and (ii) means for absorbing light of said certain frequency (color) emanating from those subareas corresponding to the discrete segmented images to be blocked from view.

28. The apparatus as in claim 27 wherein said color absorbing means includes a multi-element 90° nematic type liquid crystal shutter with individually activatable elements commensurate in extent with the subareas and having an appropriate guest-host dye.

29. The apparatus as in claim 17 wherein said masking means comprises means for blocking light corresponding to said other segmented images and transmitting through said subareas corresponding to said other segmented images, light not corresponding to said other segmented images.

30. Apparatus for use in a holographic display comprising a recording medium having a recording area with a plurality of segmented holographic images stereographically recorded in spatially separated medium subareas, each of said segmented images comprising only portions of said image visible from within a viewing cell configured with a transparent opening corresponding to the respective subarea and with imaginary, opaque segmenting planes extending away from the medium with respect to a viewer.

31. The apparatus as in claim 30 wherein the recording medium is an image plane master.

32. A process for providing in a recording medium segmented holographic images positioned within, and segmented to correspond to, respective subareas of a recording medium area, the process comprising the steps of (i) constructing graphically a plurality of viewing cells having transparent cell openings corresponding to the respective subareas and opaque segmenting cell sides extending away from the opening with respect to a viewer, (ii) generating a sequence of 2-D perspective representations of the images positioned within respective viewing cells, the representations corresponding to vantage points traversing the display area, said generating step including removing from each representation all image parts not observable through the cell opening from the respective vantage point by virtue of the segmenting cell sides, and eliminating from each representation the opaque segmenting cell sides, and (iii) recording stereographically the plurality of 2-D representations in the holographic recording medium in sequential order.

* * * * *